United States Patent [19]

Ninomiya et al.

[11] Patent Number: 6,077,980
[45] Date of Patent: Jun. 20, 2000

[54] PROCESS FOR PRODUCING POLYHYDRIC ALCOHOL

[75] Inventors: Teruyuki Ninomiya; Toshio Watanabe; Takaki Ikebe; Atsushi Iwamoto, all of Okayama-ken, Japan

[73] Assignee: Mitsubishi Gas Chemical Company, Inc., Tokyo, Japan

[21] Appl. No.: 09/118,419

[22] Filed: Jul. 17, 1998

[30] Foreign Application Priority Data

Aug. 7, 1997 [JP] Japan .................................. 9-213480

[51] Int. Cl.$^7$ ........................... C07C 29/38; C07C 31/22; C07C 47/21
[52] U.S. Cl. ............................................. 568/853
[58] Field of Search ............................................. 568/853

[56] References Cited

U.S. PATENT DOCUMENTS

| | | | |
|---|---|---|---|
| 3,975,450 | 8/1976 | Palmer et al. | 260/635 |
| 4,514,578 | 4/1985 | Immel et al. | 568/853 |
| 5,608,121 | 3/1997 | Ninomiya et al. | 568/852 |

FOREIGN PATENT DOCUMENTS

| | | |
|---|---|---|
| 0 708 073 | 4/1996 | European Pat. Off. . |
| 56-079632 | 6/1981 | Japan . |
| 63-139141 | 6/1988 | Japan . |

OTHER PUBLICATIONS

Terelak et al., Przem. Chem. (1994), 73(8), 296–7.

L. Cairate et al., "On the intermediates in the synthesis of trimethylolpropane", La Chemica E L'Industria, vol. 63, No. 11, pp. 723–725, Nov. 1981.

*Primary Examiner*—Laura L. Stockton
*Attorney, Agent, or Firm*—Frishauf, Holtz, Goodman, Langer & Chick/, P.C.

[57] ABSTRACT

A process for producing a polyhydric alcohol which comprises subjecting formaldehyde and a specific aliphatic aldehyde to an aldol condensation reaction in the presence of a base catalyst, and then subjecting the resultant reaction product to a crossed Cannizzaro reaction, while separating 2-alkenal formed as a byproduct during the aldol condensation reaction, prior to the completion of the crossed Cannizzaro reaction. Also a process for producing a polyhydric alcohol which comprises reacting formaldehyde with a 2-alkenal, such as that obtained in the aldol condensation reaction, in the presence of a base catalyst, then subjecting the resultant reaction product and a specific aliphatic aldehyde to an aldol condensation reaction, and subsequently subjecting the resultant reaction product to a crossed Cannizzaro reaction. The processes provide a polyhydric alcohol in high selectivity with a minimum excess of formaldehyde, without substantially by-producing a 2-alkenal.

14 Claims, No Drawings

PROCESS FOR PRODUCING POLYHYDRIC ALCOHOL

BACKGROUND OF THE INVENTION

1. Field of the Invention

The present invention relates to a process for producing a polyhydric alcohol by reacting an aliphatic aldehyde with formaldehyde which alcohol is useful as a raw material for polyester resins, alkyd resins, polyurethane resins, polycarbonate resins, plasticizers, surfactants, lubricating oils, basis for cosmetics, reactive monomers and the like.

2. Description of the Related Arts

There is described, as a process for producing a polyhydric alcohol, a two-stage reaction process in which an aliphatic aldehyde and formaldehyde are subjected to an aldol condensation reaction, and subsequently to a crossed Cannizzaro reaction each in the presence of a base catalyst, in Japanese Patent Application Laid-Open Nos.139141/1988 (Sho 63), 162538/1983 (Sho 58), etc., said aliphatic aldehyde being represented by the following formula (I):

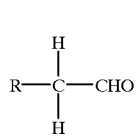

wherein R is a hydrogen atom or a straight-chain or branched aliphatic hydrocarbon group having 1 to 4 carbon atoms.

The above-mentioned two-stage reaction process is based on the premise that the objective polyhydric alcohol is produced in combination with a formic acid salt. Examples of the base catalyst to be used in said process include a hydroxide of any of alkali metals and alkaline earth meals and a carbonate of any of the above-mentioned metals. The catalyst is exemplified by sodium hydroxide, potassium hydroxide, calcium hydroxide, sodium carbonate, potassium carbonate, calcium carbonate, and tertially amines such as trimethylamine, triethylamine, and tributylamine.

In general, a base catalyst comprising sodium hydroxide or calcium hydroxide is used in the process for producing a polyhydric alcohol by the reaction of an aliphatic aldehyde with formaldehyde. However, in order to obtain an objective polyhydric alcohol in high selectiyity in the presence of the base catalyst comprising sodium hydroxide or calcium hydroxide, it is necessary to use formaldehyde in a large excess against the aliphatic aldehyde. In addition, in the case where such a large excess of formaldehyde is used, unless the reaction is carried out in a reaction system diluted with water, large amounts of byproducts are formed, thereby making it impossible to obtain the objective polyhydric alcohol in high selectivity.

There is also known a process for the production of a polyhydric alcohol by two-stage reaction process in which an aliphatic aldehyde and formaldehyde are subjected to an aldol condensation reaction, and subsequently to a crossed Cannizzaro reaction each in the presence of a carbonate catalyst. The process, however, leads to the by-production of about 10 mol % of 2-alkenals that are low in added values. Thus in order to suppress the by-production, it is also necessary to use formaldehyde in a large excess against the aliphatic aldehyde.

The aforestated process that uses a large excess of formaldehyde involves the problem such that the production process is made intricate, since it is required to recover the used excess of formaldehyde from the viewpoints of economy and the influence of wastes and the like upon the environment.

In view of the above, a general object of the present invention is to provide a process for producing a polyhydric alcohol by subjecting an aliphatic aldehyde and formaldehyde to an aldol condensation reaction, and subsequently to a crossed Cannizzaro reaction, which process is characterized in that the objective polyhydric alcohol is produced in high selectivity using a slight excess of formaldehyde against the theoretical molar amount of the aliphatic aldehyde without dilution of the reactants with water.

SUMMARY OF THE INVENTION

Under such circumstances intensive research and investigation were made by the present inventors on the process for the production of a polyhydric alcohol involved with the above-mentioned subject. As a result, it has been found that an objective polyhydric alcohol is obtained in high selectivity by carrying out an aldol condensation reaction in the presence of a catalyst comprising a carbonate as a principal ingredient, and subsequently carrying out a crossed Cannizzaro reaction, while separating 2-alkenal which has been formed as a byproduct during the aldol condensation reaction, prior to the completion of the crossed Cannizzaro reaction; or by firstly reacting the 2-alkenal thus separated with formaldehyde in the presence of a base catalyst, and subsequently reacting formaldehyde with the resultant reaction liquid which is incorporated with an aliphatic aldehyde.

Specifically, the present invention relates to a process for producing a polyhydric alcohol which comprises subjecting formaldehyde and an aliphatic aldehyde represented by the general formula (I)

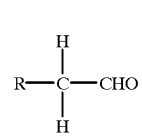

wherein R is a hydrogen atom or a straight-chain or branched aliphatic hydrocarbon group having 1 to 4 carbon atoms, to an aldol condensation reaction in the presence of a base catalyst comprising a carbonate as a principal ingredient, and subsequently subjecting the resultant reaction product to a crossed Cannizzaro reaction, while separating 2-alkenal which has been formed as a byproduct during said aldol condensation reaction prior to the completion of said crossed Cannizzaro reaction, said 2-alkenal being represented by the general formula (II):

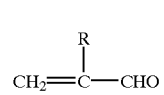

wherein R is as previously defined.

The present invention also relates to a process for producing a polyhydric alcohol which comprises reacting formaldehyde with a 2-alkenal represented by the general formula (II):

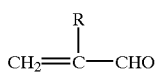
(II)

wherein R is as previously defined, in the presence of a base catalyst comprising a carbonate as a principal ingredient, thereafter subjecting the resultant reaction product and an aliphatic aldehyde to an aldol condensation reaction, and subsequently subjecting the resultant reaction product to a crossed Cannizzaro reaction.

DESCRIPTION OF THE PREFERRED EMBODIMENTS

The reaction of an aliphatic aldehyde with formaldehyde for the purpose of producing a polyhydric alcohol according to the present invention is a two-stage reaction including the aldol condensation reaction and the crossed Cannizzaro reaction in the presence of a base catalyst comprising a carbonate as a principal ingredient, and said reaction is represented by the following reaction formulae including the main reaction and the side reaction.

The following reaction formulae apply to a typical reaction example of the present invention in the case where n-butylaldehyde (hereinafter referred to as "NBAL") is reacted with trimethylol propane (hereinafter referred to as "TMP").

(1) Aldol condensation reaction

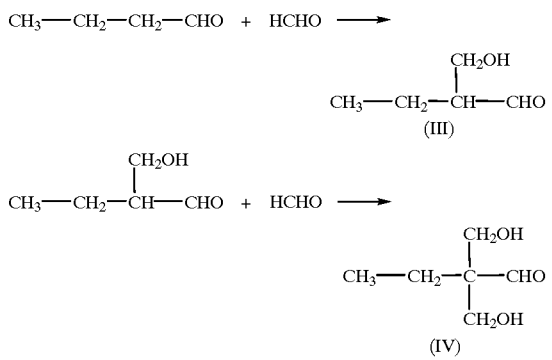

(2) Crossed Cannizzaro reaction

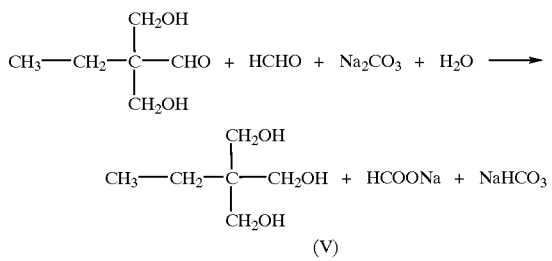

(3) Reaction by which hydrogencarbonate is converted into carbonate

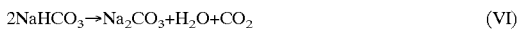

$2NaHCO_3 \rightarrow Na_2CO_3 + H_2O + CO_2$ (VI)

The carbonate, which is a catalyst and a reactional substance in the crossed Cannizzaro reaction, is consumed as a formic acid salt in the reaction system.

The aliphatic aldehyde represented by the general formula (I) according to the present invention is that having at least two hydrogen atoms at the α-position, and is exemplified by propionaldehyde, n-butyhaldehyde, acetaldehyde, pentanal and hexanal. At least two compounds among them may be used in the form of a mixture as starting raw materials.

The formaldehyde to be used in the process according to the present invention may be an aqueous solution of formaldehyde or solid paraformaldehyde, and an appropriate formaldehyde is selected for use according to the objective polyhydric alcohol.

The amount of the formaldehyde to be used in the present process varies depending upon the type of the objective polyhydric alcohol in terms of the theoretical molar amount of formaldehyde. For example, in the case where the objective TMP is produced by the reaction between formaldehyde and NBAL in which R in the general formula (I) is an ethyl group ($CH_3CH_2$) at the theoretical molar ratio of formaldehyde to the NBAL being 3.0, the practical molar ratio thereof is 3 to 6.

The base catalyst to be used in the aldol condensation reaction and the crossed Cannizzaro reaction according to the present invention, comprises a carbonate as a principal ingredient. As shown by the reaction formula (V), the compound to be consumed in the course of the crossed Cannizzaro reaction is a carbonate, and a hydrogencarbonate which is formed in the course of the crossed Cannizzaro reaction is converted into the carbonate as shown by the reaction formula (VI).

The aforestated base catalyst may be a carbonate or a mixture of a carbonate and a hydrogencarbonate that are usually available on the market as industrial chemicals. Alternatively the catalyst may be produced starting from the hydrogencarbonate that has been formed by the oxidation or hydrolysis of a formic acid salt. The carbonate may be the salt of any of sodium, potassium, lithium, calcium and ammonium, of which the sodium salt is most general in the case of industrially performing the process of the present invention.

With regard to the amount of the base catalyst to be used in the reaction, the molar ratio of the base expressed in terms of a hydrogencarbonate to an aliphatic aldehyde represented by the general formula (I), is 1 to 2. In order to obtain the objective polyhydric alcohol in high selectivity by suppressing the formation of by-products, the molar ratio needs to be regulated in compliance with the type of the aliphatic aldehyde to be used as a starting raw material. For example, the molar ratio thereof is 1.0 to 1.5 in the case of the aliphatic aldehyde being NBAL, and it is 1.0 to 1.6 in the case of the aliphatic aldehyde being acetaldehyde.

The temperature of the reaction between the aliphatic aldehyde and formaldehyde in the process of the present invention is usually 45 to 120° C., preferably 60 to 110° C., and the optimum reaction temperature varies depending upon the type of the aliphatic aldehyde to be used in the reaction.

For example, in the case of producing pentaerythritol (hereinafter referred to as "PE") from formaldehyde and acetaldehyde, the reaction temperature is 50 to 105° C. In the case of producing TMP from formaldehyde and NBAL, it is preferable to set the aldol condensation reaction temperature on 65 to 110° C., distil away 2-ethylacrylaldehyde (2-ethylacrolein) from the reaction system, and thereafter mature the reactants in the reaction system at 95 to 110° C. for 10 to 30 minutes to complete the crossed Cannizzaro reaction. It is also preferable in this case to pressurize the inside of the reaction system by means of an inert gas such as nitrogen to maintain the reaction temperature at a prescribed level.

The process for producing a polyhydric alcohol according to the present invention is the process in which the aldol condensation reaction is carried out in the presence of a base catalyst comprising a carbonate as a principal ingredient; a 2-alkenal which is by-produced in the aldol condensation reaction is separated and recovered outside the reaction system, simultaneously with the main reaction on the way or separately from the main reaction; and thereafter the crossed Cannizzaro reaction is completed.

In the process of the present invention, the aldol condensation reaction as the first stage reaction and the crossed Cannizzaro reaction as the second stage reaction may be put into practice under the reaction conditions distinguished from each other, or in the same reactor in a consecutive manner without distinguishing from each other.

The 2-alkenal represented by the general formula (II) is formed by the dehydration reaction of the alkanal in which one mol of formaldehyde is added to an aliphatic aldehyde in the aldol condensation reaction in the reaction formula (III). It is preferable that the 2-alkenal be separated and recovered from the reaction system after the addition of the aliphatic aldehyde and prior to the completion of the crossed Cannizzaro reaction.

That is to say, it is preferable to separate the 2-alkenal while the molar consumption ratio of the base catalyst to the aliphatic aldehyde is in the range of 0.50 to 0.95. The separation and recovery of the 2-alkenal are readily practicable by means of distillation under vacuum, atmospheric, or increased pressure. The loss due to the side reaction of 2-alkenal can be prevented by removing the by-produced 2-alkenal outside the reaction system prior to the completion of the crossed Cannizzaro reaction. The base catalyst comprising a carbonate as a principal ingredient is converted into a formic acid salt in the crossed Cannizzaro reaction, and thus the molar consumption ratio of the base catalyst corresponds to the molar formation ratio of the formic acid salt.

Since the base catalyst to be used in the process according to the present invention comprises a carbonate as a principal ingredient and further, the reaction in which the hydrogencarbonate is converted to the carbonate as shown by the reaction formula (VI) takes place simultaneously with the crossed Cannizzaro reaction as the second stage reaction the second stage reaction is accompanied by the generation of gaseous carbon dioxide at the time of reaction. It is preferable, therefore, that the reaction be carried out discontinuously or continuously, while discharging outside the reaction system, low boiling 2-alkenal represented by the general formula (II) as well as the gaseous carbon dioxide.

For example, in the case of producing TMP by the reaction of NBAL with formaldehyde, there are usable a method comprising the steps of mixing at first, an aqueous solution of formaldehyde and an aqueous solution of the base catalyst comprising a carbonate as a principal ingredient, and then adding NBAL dropwise at a constant rate into the resultant aqueous mixture; and a method comprising the addition of NBAL and the base catalyst in the aqueous solution of formaldehyde.

In the case of a multi-stage continuous reaction system, the 2-alkenal thus recovered can be taken out from a second or third stage reaction kettle and thereafter circulated through a first stage reaction kettle, whereas in the case of a batchwise reaction system, the 2-alkenal thus recovered can be circulated to the next reaction system. With regard to the method for adding the 2-alkenal, prior to the addition of an aliphatic aldehyde as a starting raw material, the 2-alkenal which has been recovered in the preceding reaction along with the base catalyst and formaldehyde is added to an aldol condensation reactor. By virtue of the above-mentioned adding method, it is possible to react 2-alkenal in favorable selectivity, since it follows that the 2-alkenal which is inferior in reactivity to an aliphatic aldehyde is reacted with large excesses of the base catalyst and formaldehyde. That is to say, the objective polyhydric alcohol is produced in high selectivity by reacting the 2-alkenal prior to the addition of the aliphatic aldehyde as a starting raw material to the reaction system, and also by recycling the 2-alkenal through the aldol condensation reaction system.

As the 2-alkenal to be used for the foregoing reaction, there is usable the 2-alkenal which is recovered in the refining distillation step of the objective polyhydric alcohol, in addition to the 2-alkenal which is separated and recovered in the aforesaid aldol condensation reaction step.

There are available several methods for isolating the objetive polyhydric alcohol from the reaction liquid thus obtained, for example, a method comprising the steps of firstly neutralizing the excess alkali remaining in the resultant reaction liquid by the use of formic acid; subsequently distilling away the residual formaldehyde under a pressure of 0.5 to 2.5 $kg/cm^2G$; and thereafter usually extracting with a solvent or recrystallizing the objetive polyhydric alcohol. However, the aforesaid method varies in its procedures depending upon the physical properties of the objective polyhydric alcohol, especially difference in solubility in water and the like properties.

In the case of producing TMP, for example, the objective TMP is separated from a formic acid salt by means of solvent extraction. The solvent to be used effectively therein may be the same as a starting raw material, that is, NBAL, or different therefrom including a ketone exemplified by methyl ethyl ketone and methyl isobutyl ketone, an alcohol exemplified by isobutyl alcohol and isopropyl alcohol, an ester exemplified by butyl acetate, and a mixture of at least two of them.

In the case of producing pentaerythritol (hereinafter referred to as "PE") from fomaldehyde and acetaldehyde in which R is a hydrogen atom in the general formula (I), the resultant reaction liquid is concentrated, cooled and subjected to crystallization and separation repeatedly to separate PE from the formic acid salt in the aqueous solution by means of a solid-liquid separation. The PE thus separated in the form of a cake is washed with water and dried into a finished product.

On the other hand, the formic acid salt that has been separated into a water phase is concentrated and recovered as a byproduct by a conventional method, after a treatment with activated carbon as a preliminary treatment for removing organic impurities other than the formic acid salt or without any preliminary treatment. Alternatively, the formic acid salt is coverted into a base compound comprising a hydrogencarbonate as a principal ingredient in the presence or absence of oxygen molecules in the presence of a noble metal catalyst or a nickel catalyst. Thus the formic acid is recovered in the form of a base compound.

According to the present invention, in the process for producing a polyhydric alcohol by reacting an aliphatic aldehyde with formaldehyde using a base catalyst comprising a carbonate as a principal ingredient, it is possible to easily produce the objective polyhydric alcohol in high selectivity and high efficiency by recycling the by-produced 2-alkenal low in an added value, whereby new byproduction of said 2-alkenal is substantially prevented.

Consequently, the process according to the present invention is industrially advantageous to a great extent, since it enables a high-quality polyhydric alcohol to be easily produced in high yield from an aliphatic aldehyde and formaldehyde without discharging outside the reaction system, except for a minimum requirement, the 2-alkenal low in an added value which has heretofore been inevitably by-produced and discharged.

In the following, the present invention will be described in more detail with reference to comparative examples and working examples, which however shall not limit the present invention thereto.

In the following working examples and comparative examples, the selectivity to the objective polyhydric alcohol (on the basis of the consumed aldehyde) is the molar ratio of the production of the objective polyhydric alcohol to the total consumption of an aliphatic aldehyde and 2-alkenal.

EXAMPLE 1

[Preparation of trimethylol propane (TMP) from n-butyhaldehyde (NBAL) and formaldehyde]
{First stage reaction}

In a 30 l tank type reactor were placed under mixing, 8200 g (109.2 moles) of aqueous solution of formaldehyde having a concentration of 40% by weight and 9548 g (37.5 moles) of a basic aqueous solution containing sodium hydrogencarbonate and sodium carbonate in a molar ratio of 2:98 and having a concentration of 33% by weight expressed in terms of sodium hydrogencarbonate. Then the resultant mixture in the reactor was pressurized up to 1 kg/cm$^2$G by means of nitrogen gas, and thereafter heated to raise the temperature thereof up to 80° C. under stirring. Then 2464 g (34.1 moles) of NBAL was added in the mixture at a constant rate over a period of 45 minites, while the temperature thereof was gradually raised from 80° C. up to a highest controlled temperature of 90° C. Subsequently, the temperature thereof was raised to 98° C. at a constant pressure of 1 kg/cm$^2$G, and the reaction was continued for 15 minites, while $CO_2$ which was generated during the course of the reaction was discharged outside the reaction system at every necessary time. Thereafter the temperature and pressure in the reactor were gradually lowered, and the reaction was continued for further 10 minutes, while 2-ethylacrolein (hereinafter referred to as "ECR") as a low boiling distillate and a part of water as an azeotropic component together with the generated $CO_2$ were distilled away from the top portion of the reactor to recover ECR, and the molar consumption ratio of the base catalyst to NBAL was maintained in the range of 0.5 to 0.9. The amount of the distillate was 620 g, in which the amount of the ECR was 495.6 g (5.90 moles) including that dissolved in water. After the recovery of the ECR, the reaction was continued at 98 to 100° C. for a further 30 minutes. The amount of $CO_2$ that was discharged throughout the reaction was 820 g (18.63 moles ). As a result of an analysis of 18770 g of the remaining reaction liquid, said liquid contained 17.07% by weight of TMP, and the selectivity to TMP (on the basis of the aldehyde consumed) was 84.7 mol %.
{Second stage reaction}

In a tank type reactor were placed under mixing, 6775 g (90.24 moles) of aqueous solution of formaldehyde having a concentration of 40% by weight and 7896 g (31.02 moles ) of a basic aqueous solution containing sodium hydrogencarbonate and sodium carbonate in a molar ratio of 2:98 and having a concentration of 33% by weight expressed in terms of sodium hydrogencarbonate. Then the resultant mixture in the reactor was pressurized up to 1 kg/cm$^2$G by means of nitrogen gas, and thereafter heated to raise the temperature thereof up to 80° C. under stirring. Then in the resultant mixture were added the ECR phase and the water phase that had been recovered in the first stage reaction in a total amount of 620 g and then 2035 g (28.2 moles) of NBAL at a constant rate over a period of 45 minites, while the temperature thereof was gradually raised from 80° C. up to a highest controlled temperature of 98° C . After the addition of the NBAL, the reaction was continued for 10 minutes, while the pressure and temperature in the reaction system were maintained at 1 kg/cm$^2$ and 98° C., respectively, and $CO_2$ which was generated during the course of the reaction was discharged outside the reaction system at every necessary time. Thereafter the pressure in the reactor was gradually lowered, and the reaction was continued for further 30 minites, while ECR and a part of water as an azeotropic component together with the generated $CO_2$ were distilled away from the top portion of the reactor to recover ECR, and the molar consumption ratio of the base catalyst to NBAL was maintained in the range of 0.5 to 0.9. The amount of the distillate was 654 g, in which the amount of the ECR was 498.8 g (5.94 moles) including that dissolved in water. After the recovery of the ECR, the reaction was continued at 98 to 100° C. for further 30 minutes. As a result of analysis of 16000 g of the remaining reaction liquid, said liquid contained 20.88% by weight of TMP, and the selectivity to TMP (on the basis of the aldehyde consumed) was 88.4 mol %.
{Third stage reaction}

In a tank type reactor were placed under mixing, 6775 g (90.24 moles) of aqueous solution of formaldehyde having a concentration of 40% by weight and 7896 g (31.02 moles) of a basic aqueous solution containing sodium hydrogencarbonate and sodium carbonate in a molar ratio of 2:98 and having a concentration of 33% by weight expressed in terms of sodium hydrogencarbonate. Then the resultant mixture in the reactor was pressurized up to 1 kg/cm$^2$G by means of nitrogen gas, and thereafter heated to raise the temperature thereof up to 80° C. under stirring. Then in the resultant mixture were added the ECR phase and the water phase that had been recovered in the second stage reaction in a total amount of 654 g (5.94 moles as ECR) and then 2035 g (28.2 moles) of NBAL at a constant rate over a period of 45 minutes. Thereafter the reaction was carried out in the same manner as in the second stage reaction. The amount of the ECR that was recovered in the aforesaid reaction was 496.5 g (5.91 moles) including that dissolved in water. The amount of the $CO_2$ that was discharged throughout the reaction was 675 g. As a result of analysis of 16080 g of the remaining reaction liquid, said liquid contained 21.20% by weight of TMP, and the selectivity to TMP (on the basis of the aldehyde consumed) was 90.0 mol %.

COMPARATIVE EXAMPLE 1

[2-alkenal was recovered at a stage in which the molar consumption ratio of the base catalyst was 0.95 or more]

In the same manner as in the first stage reaction of Example 1, in a tank type reactor were placed under mixing, 8200 g (109.2 moles) of aqueous solution of formaldehyde having a concentration of 40% by weight and 9548 g (37.5 moles) of a basic aqueous solution containing sodium hydrogencarbonate and sodium carbonate in a molar ratio of 2:98 and having a concentration of 33% by weight expressed in terms of sodium hydrogencarbonate. Then the resultant mixture in the reactor was pressurized up to 1 kg/cm$^2$G by means of nitrogen gas, and thereafter heated to raise the temperature thereof up to 80° C. under stirring. Then 2464 g (34.1 moles)of NBAL was added in the mixture at a constant rate over a period of 45 minites, while the temperature thereof was gradually raised from 80° C. up to a highest controlled temperature of 98° C. After the addition of the NBAL, the reaction was continued for 10 minutes, while the pressure and temperature in the reaction system were maintained at 1 kg/cm² and 98° C., respectively. Thereafter the pressure in the reactor was gradually lowered, and the reaction was continued for further 30 minutes, while the by-produced ECR was not recovered, and $CO_2$ which was generated during the course of the reaction was discharged outside the reaction system at every necessary time.

After the confirmation of the molar consumption ratio of the base catalyst to NBAL being at least 0.95, by-produced ECR was recovered in a recovery amount of 495.6 g (5.90 moles). The amount of $CO_2$ that was discharged throughout the reaction was 813 g. As a result of analysis of 19400 g of the remaining reaction liquid, said liquid contained 18.02% by weight of TMP, and the selectivity to TMP (on the basis of the aldehyde consumed) was 76.4 mol %.

COMPARATIVE EXAMPLE 2

[2-alkenal was reacted after the reaction between an aliphatic aldehyde and formaldehyde]

In a tank type reactor were placed under mixing, 6775 g (90.24 moles) of aqueous solution of formaldehyde having a concentration of 40% by weight and 7896 g (31.02 moles) of a basic aqueous solution containing sodium hydrogencarbonate and sodium carbonate in a molar ratio of 2:98 and having a concentration of 33% by weight expressed in terms of sodium hydrogencarbonate. Then the resultant mixture in the reactor was pressurized up to 1 kg/cm²G by means of nitrogen gas, and thereafter heated to raise the temperature thereof up to 80° C. under stirring. Then in the resultant mixture was added 2034 g (28.2 moles) of NBAL at a constant rate over a period of 45 minutes, and thereafter were continuously added the recovered ECR phase and water phase in a total amount of 630 g including 495.6 g (5.90 moles) of ECR. Subsequently the reaction was carried out in the same manner as in the second stage reaction of Example 2.

As a result, the total amount of the distillate containing water was 660 g, in which the amount of the recovered ECR was 498.1 g(5.93 moles) After the recovery of the ECR, the reaction was further continued at 98 to 100° C. for 30 minutes. As a result of analysis of 16060 g of the remaining reaction liquid, said liquid contained 20.10% by weight of TMP, and the selectivity to TMP (on the basis of the aldehyde consumed) was 85.4 mol %.

What is claimed is:

1. A process for producing a polyhydric alcohol which comprises subjecting formaldehyde and at least one aliphatic aldehyde to an aldol condensation reaction in the presence of a base catalyst comprising a carbonate as a principal component, said aliphatic aldehyde being represented by the formula (I):

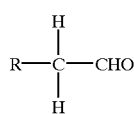

(I)

wherein R is a hydrogen atom or a straight-chain or branched aliphatic hydrocarbon group having 1 to 4 carbon atoms; and subsequently subjecting the resultant reaction product to a crossed Cannizzaro reaction, while separating a 2-alkenal which is formed as a byproduct during said aldol condensation reaction and prior to the completion of said crossed Cannizzaro reaction, said 2-alkenal being represented by the formula (II):

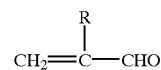

(II)

wherein R is as defined above, wherein said 2-alkenal formed during the aldol condensation reaction as a byproduct and represented by the formula (II), is separated while the molar consumption ratio of the base catalyst to the aliphatic aldehyde is 0.50 to 0.95.

2. A process for producing a polyhydric alcohol which comprises reacting formaldehyde with a 2-alkenal represented by the formula (II):

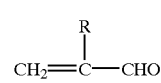

(II)

wherein R is a hydrogen atom or a straight-chain or branched aliphatic hydrocarbon group having 1 to 4 carbon atoms, in the presence of a base catalyst comprising a carbonate as a principal component; thereafter subjecting the resultant reaction product and at least one aliphatic aldehyde to an aldol condensation reaction, said aliphatic aldehyde being represented by the formula (I):

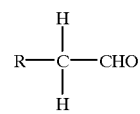

(I)

wherein R is as defined above; and subsequently subjecting the resultant reaction product to a crossed Cannizzaro reaction.

3. The process for producing a polyhydric alcohol according to claim 2, wherein said 2-alkenal is formed in a process, which comprises subjecting formaldehyde and an aliphatic aldehyde to an aldol condensation reaction in the presence of a base catalyst comprising a carbonate as a principal component, said aliphatic aldehyde being represented by the formula (I):

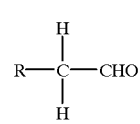

(I)

wherein R is a hydrogen atom or a straight-chain or branched aliphatic hydrocarbon group having 1 to 4 carbon atoms; and subsequently subjecting the resultant reaction product to a crossed Cannizzaro reaction, while separating a 2-alkenal which is formed as a byproduct during said aldol condensation reaction and prior to the completion of said crossed Cannizzaro reaction, said 2-alkenal being represented by the formula (II):

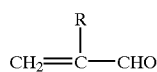

(II)

wherein R is as defined above.

4. The process for producing a polyhydric alcohol according to claim 2, wherein said 2-alkenal formed as a byproduct during the aldol condensation reaction is separated prior to the completion of the crossed Cannizzaro reaction.

5. The process for producing a polyhydric alcohol according to claim 1, wherein the aliphatic aldehyde is n-butyraldehyde, and trimethylol propane is produced from said formaldehyde and said n-butyraldehyde.

6. The process for producing a polyhydric alcohol according to claim 2, wherein the aliphatic aldehyde is n-butyraldehyde, and trimethylol propane is produced from said formaldehyde and said n-butyraldehyde.

7. The process for producing a polyhydric alcohol according to claim 1, wherein the aliphatic aldehyde is at least one aldehyde selected from the group consisting of propionaldehyde, n-butyraldehyde and acetaldehyde.

8. The process for producing a polyhydric alcohol according to claim 1, wherein the aliphatic aldehyde is at least one aldehyde selected from the group consisting of pentanal and hexanal.

9. The process for producing a polyhydric alcohol according to claim 1, wherein the aliphatic aldehyde is n-butyraldehyde and the molar ratio of the formaldehyde to the n-butyraldehyde is 3 to 6.

10. The process for producing a polyhydric alcohol according to claim 1, wherein the carbonate is hydrogen carbonate and a molar ratio of the hydrogen carbonate to the aliphatic aldehyde is 1 to 2.

11. The process for producing a polyhydric alcohol according to claim 1, wherein the aldol condensation reaction is carried out at a temperature of 45 to 120° C.

12. The process for producing a polyhydric alcohol according to claim 10, wherein the aliphatic aldehyde is n-butyraldehyde; the molar ratio of the hydrogen carbonate to the aliphatic aldehyde is 1.0 to 1.5; and the aldol condensation reaction is carried out at a temperature of 65 to 110° C.

13. The process for producing a polyhydric alcohol according to claim 12, wherein the molar ratio of the formaldehyde to the n-butyraldehyde is 3 to 6.

14. The process for producing a polyhydric alcohol according to claim 10, wherein the aliphatic aldehyde is acetaldehyde; the molar ratio of the hydrogen carbonate to the aliphatic aldehyde is 1.0 to 1.6; and the aldol condensation reaction is carried out at a temperature of 50 to 105° C.

* * * * *